United States Patent
Takada et al.

(10) Patent No.: US 6,924,136 B2
(45) Date of Patent: Aug. 2, 2005

(54) CYCLODEXTRIN GLUCANOTRANSFERASE AND ITS METHOD OF MANUFACTURE

(75) Inventors: Masayasu Takada, Fuji (JP); Takahiro Ide, Fuji (JP); Takeshi Yamamoto, Fuji (JP); Takehiro Unno, Fuji (JP); Yoshimi Watanabe, Sunto-gun (JP); Hironobu Sone, Fuji (JP); Mikio Yamamoto, Fuji (JP)

(73) Assignee: Nihon Shokuhin Kako Co. Ltd., Tokyo (JP)

( * ) Notice: Subject to any disclaimer, the term of this patent is extended or adjusted under 35 U.S.C. 154(b) by 0 days.

(21) Appl. No.: 10/296,129

(22) PCT Filed: May 23, 2001

(86) PCT No.: PCT/JP01/04310

§ 371 (c)(1),
(2), (4) Date: Apr. 14, 2003

(87) PCT Pub. No.: WO01/90335

PCT Pub. Date: Nov. 29, 2001

(65) Prior Publication Data

US 2003/0194796 A1 Oct. 16, 2003

(30) Foreign Application Priority Data

May 23, 2000 (JP) ........................................ 2000-151053

(51) Int. Cl.⁷ ................................................ C12N 9/10
(52) U.S. Cl. ................................. 435/193; 435/252.31
(58) Field of Search ............................... 435/193, 71.2, 435/97, 183, 252.31, 832; 536/46, 103, 124

(56) References Cited

U.S. PATENT DOCUMENTS

| | | | | |
|---|---|---|---|---|
| 4,897,472 A | * | 1/1990 | Korpela et al. | 536/46 |
| 5,238,825 A | * | 8/1993 | Oguma et al. | 435/101 |
| 5,409,824 A | | 4/1995 | Schmid | |
| 5,474,917 A | * | 12/1995 | Schulz et al. | 435/97 |
| 5,556,775 A | * | 9/1996 | Karube et al. | 435/97 |
| 5,707,833 A | * | 1/1998 | Mori et al. | 435/71.2 |
| 5,804,426 A | * | 9/1998 | Nikolov et al. | 435/193 |
| 6,004,790 A | * | 12/1999 | Dijkhuizen et al. | 435/193 |
| 6,271,010 B1 | * | 8/2001 | Andersen et al. | 435/193 |
| 6,472,192 B1 | * | 10/2002 | Schulz et al. | 435/193 |

OTHER PUBLICATIONS

Jeang C. Studies on the Production of Cyclodextrins. J of the Chinese Agricultural Chemical Society 29(4)502–512, 1991.*

Gawande B. Purification and Properties of a Novel Raw Starch Degrading Cyclomaltodextrin Glucanotransferase from Bacillus firmus. Applied Microbiol Biotechnology 51(4)504–509,1999.*

Yim, D.G. Production of Cyclodextrin from Starch . . . J of Industrial Micro & Biotech 18(6)402–405, 1997.*

Fujita et al. "Purification and Properties of Cyclodextrin Glycosyltransferase from *Bacillus* sp. AL–6". Journal of Fermentation and Bioengineering 70:3 (1990), 150–54.

Nakamura et al., "Four Aromatic Residues in the Active Center of Cyclodextrin Glucanotransferase from Alkalophilic *Bacillus* sp. 1011: Effects of Replacements on Substrate Binding and Cyclization Characteristics." Biochemistry 33:33 (1994), 9929–36.

Nielsen et al., "Phenetic diversity of alkaliphilic *Bacillus* strains: proposal for nine new species." Microbiology 141 (1995), 1745–61.

Tonkova, Alexandra. "Bacterial cyclodextrin glucanotransferase." Enzyme and Microbial Technology 22 (1998), 678–86.

* cited by examiner

*Primary Examiner*—Ralph Gitomer
(74) *Attorney, Agent, or Firm*—Jacobson Holman PLLC

(57) ABSTRACT

CGTase enzymatically acts on starch, dextrin, amylopectin, and amylose to produce primarily γ-CD, with quantities of β- and α-CD produced being smaller than the quantity of γ-CD produced, has an optimum pH of 10.5–11.0, an optimum temperature of about 60° C., a stable pH of 6–11, and temperature stability, exhibits residual activity of not less than 90 percent with a 15 minute-treatment at 50° C., is produced by culturing a *Bacillus clarkii* (for example, FERM B-7156), reacts with starch or the like to produce principally γ-cyclodextrin.

7 Claims, 3 Drawing Sheets

SEQUENCE LISTING

<160> NUMBER OF SEQ ID NOS: 1

<210> SEQ ID NO 1
<211> LENGTH: 1547
<212> TYPE: DNA
<213> ORGANISM: Bacillus clarkii 7364

<400> SEQUENCE: 1

| | | | | | | |
|---|---|---|---|---|---|---|
| tggagagagt | ttgatcctgg | ctcaggacga | acgctggcgg | cgtgcctaat | acatgcaagt | 60 |
| cgagcggacc | aaaggaagct | tgcttccgga | ggtcagcggc | ggacgggtga | gtaacacgtg | 120 |
| ggcaacctgc | cttacagact | gggataactc | cgggaaaccg | gggctaatac | cggatgaccg | 180 |
| atgggaccgc | atggtcctgt | cgtaaaagtt | gggattacta | acactgtaag | atgggcccgc | 240 |
| ggcgcattag | ctagttggtg | aggtaacggc | tcaccaaggc | gacgatgcgt | agccgacctg | 300 |
| agagggtgat | cggccacact | gggactgaga | cacggcccag | actcctacgg | gaggcagcag | 360 |
| tagggaatca | tccgcaatgg | gcgaaagcct | gacggtgcaa | cgccgcgtga | acgaggaagg | 420 |
| tcttcggatt | gtaaagttct | gttgtcaggg | aagaagaagt | gccattcgaa | yaggttggca | 480 |
| ccgtgacggt | acctgacgag | aaagcccgg | ctaactacgt | gccagcagcc | gcggtaatac | 540 |
| gtaggggca | agcgttgtcc | ggaattattg | ggcgtaaagc | gcgcgcaggc | ggtttcttaa | 600 |
| gtctgatgtg | aaagcccacg | gctcaaccgt | ggagggtcat | tggaaactgg | gagacttgag | 660 |

-continued

```
tgtaggagag gaaagtggaa ttccacgtgt agcggtgaaa tgcgtagaga tgtggaggaa      720
caccagtggc gaaggcgact ttctggccta taactgacgc tgaggcgcga aagcgtgggg      780
agcaaacagg attagatacc ctggtagtcc acgccgtaaa cgatgagtgc taggtgttag      840
gggtttcgat acccttagtg ccgcagttaa cacattaagc actccgcctg gggagtacgg      900
ccgcaaggct gaaactcaaa ggaattgacg ggggcccgca caagcagtgg agcatgtggt      960
ttaattcgaa gcaacgcgaa gaaccttacc aggtcttgac atcctctgcc actcctggag     1020
acaggacgtt ccccttcggg ggacagagtg acaggtggtg catggttgtc gtcagctcgt     1080
gtcgtgagat gttgggttaa gtcccgcaac gagcgcaacc cttgatctta gttgccagca     1140
ttgagttggg cactctaagg tgactgccgg tgacaaaccg gaggaaggtg gggatgacgt     1200
caaatcatca tgcccttat gacctgggct acacacgtgc tacaatgggt ggtacaaagg      1260
gcagcaacgc cgcgaggccg agcgaatccc agaaagccac tctcagttcg gattgcaggc     1320
tgcaactcgc ctgcatgaag ccggaattgc tagtaatcgc ggatcagcat gccgcggtga     1380
atacgttccc gggccttgta cacaccgccc gtcacaccac gagagtttgt aacacccgaa     1440
gtcggtgagg taacctttg gagccagccg ccgaaggtgg gacagatgat tgggggtgaag     1500 tcgtaacaag gtatccctac cggaaggtgc ggytggatca cctcctt                   1547
```

CYCLODEXTRIN GLUCANOTRANSFERASE AND ITS METHOD OF MANUFACTURE

This is 371 of PCT/JP01/04310 filed May 23, 2001, which claims priority to Japan Application 2000-151053 filed May 23, 2000.

FIELD OF THE INVENTION

The present invention relates to cyclodextrin glucanotransferase (EC 2.4.1.19, referred to as "CGTase" hereinafter), a method of manufacturing the same, and a method of manufacturing cyclodextrin (referred to as "CD" hereinafter) employing the same.

BACKGROUND OF THE INVENTION

CGTase (EC 2.4.1.19) is an enzyme functioning on α-1,4-glucans such as starches to produce cyclodextrins (CD), which are cyclic α-1,4-glucans, through its intramolecular transfer activity. The degree of polymerization of the CDs produced by CGTase is chiefly 6–8, with these products being referred to as α-, β and γ-CD, respectively. In addition to this CD-producing reaction, CGTase catalyzes coupling reactions (the ring of the CD is opened and the resulting straight-chain oligosaccharide is transferred to a receptor sugar molecule) and disproportionation reactions (a straight-chain oligosaccharide is transferred to the receptor sugar molecule) through the intramolecular transfer reaction. Further, albeit weakly, CGTase also catalyzes the hydrolysis reaction of the α-1,4-glucoside bond.

Since CDs can change chemical and physical properties of various molecules by making clathrates therewith, CGTase has achieved a position as an important enzyme in the food, pharmaceutical and cosmetic industries. Thus, beginning from the CD synthesis reaction by the *Bacillus macerans* enzyme in 1939 (E. B. Tilden and S. J. Pirt, J. Am. Chem. Soc., 63, 2900–2902, 1939), a large number of studies were conducted, including a search for bacteria producing CGTase and means of purifying the enzyme (Sumio Kitahata, Naoto Tsuyama and Shigetaka Okada, Agr. Biol. Chem., 38 (2), 387–393, 1974; Sumio Kitahata and Shigetaka Okada, Agr. Biol. Chem., 38 (12), 2413–2417, 1974; Sumio Kitahata and Shigetaka Okada, J. Jap. Soc. Starch Sci., 29 (1), 13–18, 1982; Michio Kubota, Yoshiki Matsuura, Shuzo Sakai and Yukiteru Katsube, Denpun Kagaku, 38 (2), 141–146, 1991; Lionel J. Bovetto, Daniel P. Backer, Jaques R. Villette, Philippe J. Sicard, and Stephane J-L. Bouquelet, Biotechnology and Applied Biochemstry, 15, 48–58, 1992; Shinske Fujiwara, Hirofumi Kakihara, Kim Myung Woo, Andre Lejeune, Mitsuhide Kanemoto, Keiji Sakaguchi, and Tadayuki Imanaka, Applied and environmental microbiology, 58 (12), 4016–4025, 1992; Florian Binder, Otto Huber and August Bock, Gene, 47, 269–277, 1986; Keiji Kainuma, Toshiya Takano and Kunio Yamane, Appl. Microbiol. Biotechnol., 26, 149–153, 1987; Takahiro Kaneko, Tetsuo Hamamoto and Koki Horikoshi, J. general Microbiology, 134, 97–105, 1988; Murai Makela, Pekka Mattsson, M. Eugenia Schinina, and Timo Korpela, Biotechnology and Applied biochemistry, 10, 414–427, 1988; Ernest K. C. Yu, Hiroyuki Aoki, and Masanaru Misawa, Appl. Microbiol. Biotechnol., 28, 377–379, 1988).

Based on the type of CD principally synthesized, CGTase is classified as α-CGTase, β-CGTase or γ-CGTase. Most of what has been reported in the past has related to α-, or β-CGTase. Few enzymes have been reported as being γ-CGTase (Shigeharu Mori, Susumu Hirose, Takaichi Oya, and Sumio Kitahata, Oyo Toshitsu Kagaku, 41 (2), 245–253, 1994; Yoshito Fujita, Hitoshi Tsubouchi, Yukio Inagi, Keiji Tomita, Akira Ozaki, and Kazuhiro Nakanishi, J. Fermentation and Bioengineering, 70 (3), 150–154, 1990; and Takashi Kato and Koki Horikoshi, J. Jpn. Soc. Starch Sci., 33 (2), 137–143, 1986).

Enzymes reported to be γ-CGTase is not industrially available because the quantity of γ-CD produced is not more than 5 percent, the rate of production of β-CD accelerates in the later stages of the reaction and thus the amount of β-CD produced is equal to or greater than the amount of γ-CD produced, or the amount of γ-CD produced drops precipitously at a substrate concentration of 10 percent or greater and, as a countermeasure, ethanol must be present together in the reaction solution.

On the other hand, attempts have also been made to modify the structural genes of α- or β-CGTase to improve the quantity of γ-CD produced (Akira Nakamura, Keiko Haga, and Kunio Yamane, Biochemstry, 32, 6624–6631, 1993; and Michio Kubota, Yoshiki Matsuura, Shuzo Sakai and Yukiteru Kutsume, Oyo Toshitsu Kagaku, 41 (2), 245–253, 1994). However, these are also inadequate from an industrial perspective, because even when the quantity of γ-CD produced is increased, the β-CD produced by the original activity is not decreased substantially.

Thus, although α-CD and β-CD are employed in various fields, γ-CD is currently little employed. The same is true for CD-containing syrups. CD syrups comprising principal components in the form of α-CD or β-CD are employed in various fields, while CD syrup comprising γ-CD as principal component are seldom employed.

BRIEF SUMMARY OF THE INVENTION

Accordingly, an object of the present invention is to provide a new γ-CGTase capable of predominantly producing γ-CD. A further object of the present invention is to provide a new microorganism having the ability to produce a γ-CGTase for that purpose.

A still further object of the present invention is to provide a method of manufacturing γ-CD employing the above-mentioned γ-CGTase.

The present inventors conducted a broad search of the natural world for microorganisms having the ability to produce CGTase producing γ-CD. As a result, they discovered the desired strain of bacteria having the ability to produce CGTase among bacteria belonging to the species *Bacillus clarkii*. After culturing this microorganism, producing CGTase in the cultured product, and collecting and identifying the product, it was discovered that this CGTase is a new enzyme, resulting in achieving the present invention. It was further discovered that this CGTase could be used to predominantly manufacture γ-CD, and an industrial method of manufacturing γ-CD was devised.

The present invention relates to cyclodextrin glucanotransferase having the enzymatic chemical properties listed below:

(1) Function and substrate specificity: Functioning on starch, dextrin, amylopectin or amylose to produce primarily γ-cyclodextrin, with the quantities of β- and α-cyclodextrin produced being smaller than the quantity of γ-cyclodextrin produced;

(2) Optimum pH: 10.5–11.0;

(3) Optimum temperature: Around 60° C.;

(4) Stable pH: 6–11;

(5) Temperature stability: With a 15 minute-treatment at 50° C., residual activity of not less than 90 percent is exhibited.

Further, the method of manufacturing cyclodextrin glucanotransferase of the present invention is characterized in that a microorganism belonging to the species *Bacillus clarkii* and having the ability to produce cyclodextrin glucanotransferase is cultured, cyclodextrin glucanotransferase is produced in the cultured product, and then the cyclodextrin glucanotransferase that has been produced is collected.

In the above-stated method, *Bacillus clarkii* strain 7364 (FERM BP-7156) may be employed as the microorganism belonging to the species *Bacillus clarkii* and having the ability to produce cyclodextrin glucanotransferase.

Further, the method of manufacturing cyclodextrin of the present invention is characterized in that cyclodextrin glucanotransferase produced by the species *Bacillus clarkii* is reacted with a solution comprising at least one member selected from among the group consisting of starch, dextrin, aminopectin, and amylose to produce primarily γ-cyclodextrin and the γ-cyclodextrin produced is collected.

In the method of manufacturing cyclodextrin of the present invention set forth above, the cyclodextrin glucanotransferase can be the cyclodextrin glucanotransferase of the present invention.

The present invention further relates to *Bacillus clarkii* strain 7364 (FERM BP-7156), which is a bacteria of *Bacillus clarki* species having the ability to produce cyclodextrin glucanotransferase.

Figure 1:
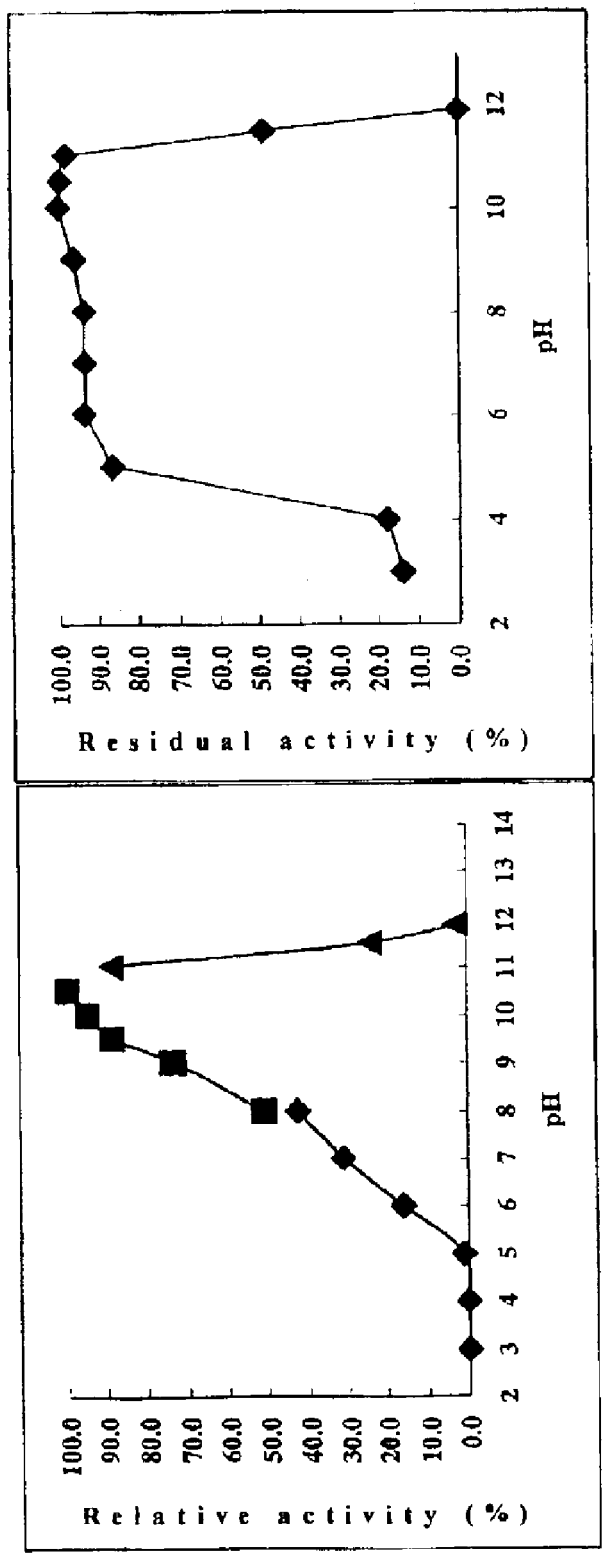
FIG. 1 is a graph showing the effect of pH on the activity of γ-CGTase derived from *Bacillus clarkii* 7364 (Blue value method).

DETAILED DESCRIPTION OF THE INVENTION (Cyclodextrin Glucanotransferase)

Table 1 gives the bacteriological properties of the strain newly discovered and separated by the present inventors.

TABLE 1

Various properties of the bacterial strain

| | |
|---|---|
| Culture temperature | 37° C. |
| Cell form | Rod-shaped microorganism (0.6–0.8 × 3–5 μm) with elongated form |
| Gram dyeing | + |
| Spores | ± |
| Motility | + |
| Colony form | Shape of colony: irregular |
| | Perimeter of colony: filamentous |
| | Colony surface protrusions: low and flat |
| | Luster: None |
| | Color: Cream |
| | Size: Φ 3–4 mm |
| | Characteristics: Colonies adhere to medium |
| Catalase | + |
| Oxidase | + |
| O/F Test | – |
| β-Galactosidase | + |
| Arginine hydrolase | – |
| Lysine decarboxylase | – |
| Ornithine decarboxylase | – |
| Use of citric acid | – |
| $H_2S$ production | – |

TABLE 1-continued

Various properties of the bacterial strain

| | |
|---|---|
| Urease | – |
| Tryptophan deamidase | – |
| Indole production | – |
| Acetoin production | + |
| Gelatinase | – |
| Nitrate reduction | – |
| Hydrolysis | Casein + |
| | Gelatin + |
| | Starch + |
| | Tween 20 – |
| | Tween 40 + |
| | Tween 60 + |
| Phenyl alanine deamidase | – |
| Growth properties | 10° C. – |
| | 40° C. + |
| | 50° C. – |
| | pH 7 – |
| | 5% NaCl + |
| | 10% NaCl + |
| Identification result | *Bacillus clarkii* |

The 16 S rDNA nucleotide sequence of this bacterial strain is shown as SEQ ID NO:1 in the sequence listing.

This bacterial strain is a motile gram-positive rod-shaped microorganism also exhibiting an extended form. It is positive for both catalase and oxidase. Although determination of the form of the spores was difficult, the impression was obtained of terminal spores on extended form extremities, and it was presumed to belong to the genus *Bacillus*. In addition, bacterial body fatty acid composition (CFA), 16 S rDNA nucleotide sequencing, and tests of utilization of saccharides were conducted. Since the fastest proliferation rate was achieved with this bacterial strain in the alkaline range and it would not grow at pH 7.0 or below, it was categorized into alkalophilic bacteria. Although it had a low homology ratio of 96.12 percent in 16 S rDNA nucleotide sequencing with previously reported Alkalophilic *Bacillus clarkii* (Preben Nielsen, Dagmar Fritze and Fergus G. Priest, Microbiology, 141, 1745–1761, 1995), it was presumed to be a related species. However, in other physiological property tests, it exhibited a good match with values reported by I. Yumoto et al. (I. Yumoto et al., Int. J. Syat. Bacteriol., 48, 565–571, 1998), and this bacterial strain was presumed to be *Bacillus clarkii*.

These results clearly show this bacterial strain to be a new bacterial species, which has been named *Bacillus clarkii* strain 7364. This bacterial strain has been deposited with Kogyo Gijutsuin Seimei Kogaku Kogyo Gijutsu Kenkyujo (currently, the Patent Organism Depositary, National Institute of Advanced Industrial Science and Technology, 1-1, 1 chome, Tsukuba Higashi, Ibaraki Prefecture, Japan) as FERM BP-7156.

To date, no other bacterial strain of *Bacillus clarkii* having the ability to produce CGTase has been reported within *Bacillus clarkii* species. Further, the related species of *B. horti* (JCM No. 9943T), *B. clarkii* (ATCC No. 700162), and *B. agaradhaerens* (ATCC No. 700163) have been confirmed not to have CGTase activity. That is, the present bacterial strain is the first bacterial strain belonging to the *Bacillus clarkii* species to have the ability to produce CGTase.

(Method of Manufacturing Cyclodextrin Glucanotransferase)

To manufacture CGTase using *Bacillus clarkii* strain 7364, the microorganism is vigorously grown and then cultured in a synthetic or natural medium comprising the carbon source, nitrogen source, inorganic salts, necessary nutrients, and the like that are necessary for the smooth production of the enzyme. Examples of carbon sources suitable for use are carbohydrates such as starches and compositional fractions thereof, baked dextrin, processed starches, starch derivatives, physically processed starches, and α-starches. Specific examples are soluble starch, corn starch, potato starch, sweet potato starch, dextrin, amylopectin, and amylose. Examples of nitrogen sources are organic nitrogen source substances such as polypeptones, casein, meat extract, yeast extract, corn steep liquor, soybeans, soybean cakes, and other extracts; inorganic nitrogen compounds such as ammonium sulfate and ammonium phosphate; and amino acids such as glutamic acid. Examples of inorganic salts suitable for use are phosphates such as monopotassium phosphate and dipotassium phosphate; magnesium salts such as magnesium sulfate; calcium salts such as calcium chloride; and sodium salts such as sodium carbonate. Culturing is desirably conducted under aerobic conditions by shake culturing or stir culturing with ventilation in a medium adjusted to greater than pH 7, preferably to within the range of pH 8 to 11, at a temperature falling within the range of 10–45° C., preferably 30–42° C. However, culturing is not specifically limited thereto and may be conducted under other conditions so long as the microorganism grows and the targeted enzyme is produced.

When cultured under the conditions as mentioned above, a substantial amount of CGTase is normally produced in the culture solution about 48 hours after the start of culturing. Next, the bacterial body is removed from the culture solution, yielding a filtered culture solution. This is desalted with an ultrafiltration membrane and concentrated, and the enzyme is recovered. The roughly purified enzyme thus obtained may be used as it is in the CD production reaction. However, as necessary, it can be employed following purification by ammonium sulfate salting out; precipitation from an organic solvent; adsorption elution by DEAE-Sephadex or butyl Toyopal; column fractionation by Sephadex, Toyopal and the like; and affinity chromatography in which γ-CD is derived as a ligand.

Methods of measuring enzyme activity are described below.

(CGTase Activity Measurement)

CGTase activity was measured at 40° or 50° C. using 50 mM glycine-NaCl—NaOH buffer solution (pH 10.0).

(Blue Value Method)

50 mg of amylose (EX-III type made by Hayashibara) was dissolved in 2 mL of 1 N NaOH overnight, neutralized with 1 N HCl, added 50 mM glycine-NaCl—NaOH buffer (pH 10.0) to 50 mL, yielding a substrate solution. A 300 µL of the substrate solution was maintained at a temperature of 40° C. for 10 minutes, 200 µL of a suitably diluted enzyme solution was added to start the reaction, and the reaction was conducted for 10 minutes at the same temperature. The reaction was then stopped by adding 4 mL of 0.2 N HCl. To the reaction solution, 4 mL of water and 500 µL of 0.02 percent I2–0.2 percent KI solution were added. The absorbance at 700 nm was measured. A control was prepared by similarly adding 0.2 N HCl and then adding an enzyme solution. One unit was defined as the quantity of enzyme reducing the absorbance at 700 nm under these conditions by 10 percent in one min. relative to the control.

(γ-CD Production Activity)

One mL of soluble starch (nacalai tesque) was dissolved in 25 mM glycine-NaCl—NaOH buffer (pH 10.0) to 10% (w/v) and heated at 50° C. for 10 minutes. A 200 µL of a suitably diluted enzyme solution was added to start the reaction, the reaction was continued for 30 minutes at the same temperature, and the reaction was stopped by adding 3 mL of 0.02 N HCl. A 20 µL of the reaction solution was subjected to HPLC and the quantity of γ-CD produced was measured. One unit was defined as the amount of enzyme producing 1 µmol/mL of γ-CD per minute under these conditions.

The HPLC conditions employed in this measurement are as follows:

| Column | YMC-pack AQ-312 (6 × 150 mm) |
|---|---|
| Solvent | 10 percent MeOH |
| Flow rate | 1.0 mL/min |
| Temp. | R. T. |
| Detection | RI |
| ATT | 7 |

A CD solution of prescribed concentration was analyzed under the above-stated conditions and a calibration curve having the following equation was obtained by calculating the correspondence between the CD content and the HPLC area.

(HPLC area)=3.092×106×(γ-CD w/v %) R2=0.999

(Analysis of Quantity of CD Produced)

The CD content in the reaction solution was analyzed by HPLC. The analysis conditions are as follows.

| HPLC Method 1 | |
|---|---|
| Column | Aminex HPX-42A (Bio-Rad Lab. 7.8 × 300 mm) |
| Solvent | H$_2$O |
| Flow rate | 0.5 mL/min |
| Temp. | 55° C. |
| Detection | RI |
| ATT | 9 |

HPLC Method 2 was identical to the method employed to analyze CD production activity.

The CD production reaction was conducted using soluble potato starch (Sigma) as a substrate.

The various enzymological properties of the CGTase obtained are given below.

A 200 µL of the enzyme (100 µg of protein) and 1.0 percent (w/v) amylose (DP 117) dissolved in various buffers of pH 3–11.9 were reacted for 10 min at 40° C. and the relative activity (Blue value method) was calculated. Further, 50 µL of enzyme solution (25 µg of protein) and 500 µL of various buffers with a pH ranging from 3 to 11.9 were combined and then left standing at 4° C. for 24 hours. After adding 2.75 mL of 50 mM glycine-NaOH buffer (pH 10.0), the residual activity was measured (FIG. 1). The results revealed that the optimum pH of the enzyme and the pH stability range were 10.5–11.0 and 6–11.0, respectively.

Figure 2:
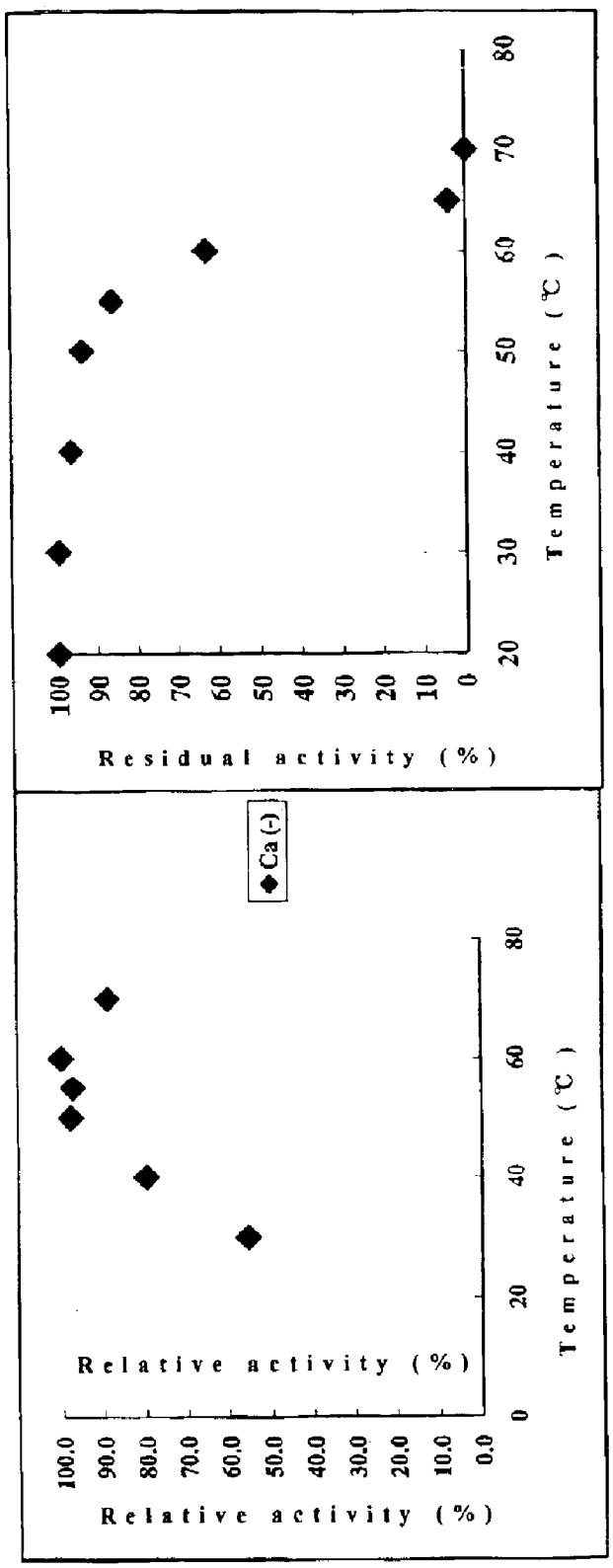
FIG. 2 is a graph showing the effect of temperature on the activity of γ-CGTase derived from *Bacillus clarkii* 7364 (Blue value method).

A 200 µL of the enzyme (100 µg of protein) and 1.0 percent (w/v) amylose (DP 117) dissolved in 50 mM glycine-NaOH buffer (pH 10.0) were reacted for 10 min at various temperatures and the relative activity (Blue value method) was calculated. Further, 20 µL of enzyme solution and 1,180 mL of 50 mM glycine-NaOH buffer (pH 10.0) were mixed and then left standing at various temperatures for 15 min. The residual activity was measured (FIG. 2). The results revealed that the optimum temperature of the enzyme and the temperature stability range were 60° C. and 30° C. or below, respectively. These results were identical for γ-CD production activity.

A comparison of the various physical properties of the enzyme in the form of the above results, the molecular weight of the enzyme, and isoelectric point examination results are compared in Table 2 to those of CGTase derived from other bacterial strains.

TABLE 2

A comparison of various physical properties with CGTase of other sources already reported

| Bacterial strain | B. Clarkii 7364 strain | B. sp. AL-6 | B. stearothermophilus | B. megaterium (F1  F2) | B. circulans (F1  F2) | B. macerans (IFO 3490) |
|---|---|---|---|---|---|---|
| Isoelectric point | 3.98 | — | 4.45 | 6.07   6.80 | 5.80   6.60 | 4.60 |
| Optimum pH | 10.5–11.0 | 7.5–10.5 | 6.0 | 5.2–6.2 | 5.2–5.7 | 5.2–5.7 |
| Optimum temp. | 60°C. | 55° C. | 70° C. | 55° C. | 55° C. | 55° C. |
| Stability (pH) | 6.0–11.0 | 5–8 | 7.0–9.2 | 7.0–10.0 | 7.0–9.0 | 8.0–10.0 |
| Stability (temp) | 30° C. | 40° C. | 50° C. | 55° C. | 55° C. | 55° C. |
| Molecular weight | 66,000 | 74,000 | 68,000 | 66,000 | — | 65,000 |
| Main product | γ | γ, β | α, β | β | β | α |

The molecular weight of CDTase derived from *Bacillus Clarkii* 7364 strain was 66,000 by SDS-PAGE and the isoelectric point thereof was 3.98 (focusing electrophoresis). (Method of Manufacturing Cyclodextrin)

CD can be manufactured with the CDTase of the present invention, for example, by adding 0.5–300 U (per gram of dry starch) of the present enzyme solution (purified enzyme or crude enzyme) to an aqueous solution comprising 1–30 percent starch (including starch or a compositional fraction thereof, dextrin, amylopectin, amylose, or some other processed starch) and conducting an enzymatic reaction for 1–96 hours at 20–60° C. from pH 4.5–12. As needed, the starch can be preheated or subjected to a liquefaction treatment for use. More γ-CD than α-CD and β-CD is contained in the sugars (syrup) prepared by the method as mentioned above. In addition to these CDs, monosaccharides such as glucose and various oligosaccharides (maltose and the like), dextrin, and the like are sometimes contained. Further, as needed, a CD having a desired single degree of polymerization can be separated (by crystallization, chromatofractionation, fermentation by yeast or the like, enzymic treatment, or the like) for use. That is, γ-CD can be separated and purified from the above-described product. Since the reaction solution obtained by the method of the present invention comprises more γ-CD than α-CD and β-CD, the γ-CD is more readily separated and purified than in prior art. In addition to the syrup obtained by the above-mentioned method, the form may be any other form such as crystals, freeze-dried product, powder, or granules.

The CD (particularly CD with a high γ-CD content or highly purified γ-CD) manufactured by the manufacturing method of the present invention can be employed in all food and drink products suited to oral consumption in the same manner as currently available CD. Examples of such food and drink products are beverages such as tea and refreshment beverages; Japanese and Western snacks such as candies, jellies, and Japanese finger foods; milk products such as yogurt and ice-cream; processed meat products such as ham and sausage; processed seafood products such as boiled fish paste and Naruto; noodles; pickled vegetables; other prepared foods; and instant foods. Further, the CD manufactured by the manufacturing method of the present invention can be added and incorporated to stabilize or emulsify fragrance materials and the like, or as an excipient or the like, to conveniently and effectively enhance the desirability and functionality thereof. Further, in addition to foods and beverages, the CD manufactured by the manufacturing method of the present invention can be employed to stabilize the active ingredients of, and emulsify, not only foods and drinks, but also pharmaceuticals, cosmetic products and the like, and as an excipient.

The method of use of the CD manufactured by the manufacturing method of the present invention is not specifically limited so long as the CD is present together in a food or drink product, pharmaceutical, or cosmetic. For example, the CD can be added simultaneously with the processing of the food or drink material serving as the base or added after completion of processing of the base food or drink product. It suffices to employ a method of addition suited to the actual conditions of the process of manufacturing the individual food product.

In the case of food and drink products, the quantity of CD added is not specifically limited so long as the base food or drink product does not lose its original flavor or aroma. Generally, a quantity added of not greater than 20 weight percent is desirable. Equal to or greater than 20 weight percent is undesirable because it is apprehended that the desirability is diminished by changing the flavor or aroma of the base food or drink product by the masking effect of the CD. In the case of pharmaceuticals and cosmetics, there is no particular limitation so long as the effect of the active ingredients is not lost; the use of not more than 50 weight percent is desirable.

The inventions disclosed in the present specification relate to inventions described in Japanese Patent Application No. 2000-151053 filed with the Japan Patent Office on May 23, 2000. The full disclosure of the Japanese patent application is expressly incorporated herein by reference.

EMBODIMENTS

The present inventions are more specifically described below through embodiments.

Embodiment 1

*Bacillus clarkii* 7364 strain (FERM BP-7156) was cultivated with shaking for 48 hours at 37° C. in a liquid medium comprising a carbon source in the form of 1.0 percent (w/v) of Neotack #30T (made by Nihon Shokuhin Kako Co., Ltd.), a nitrogen source in the form of 0.5 percent Soyflower-FT (made by Nisshin Oil Mills, Ltd.), 0.5 percent yeast extract (made by Difco), 0.1 percent $K_2HPO_4$, 0.02 percent $MgSO_4 \cdot 7H_2O$, and 0.8 percent $Na_2CO_3$. CGTase was secreted into the culture solution (Blue value method 20 U/mL culture supernatant).

The CGTase obtained was purified by affinity chromatography. The physical properties thereof are given in Table 2.

Embodiment 2

Figure 3:
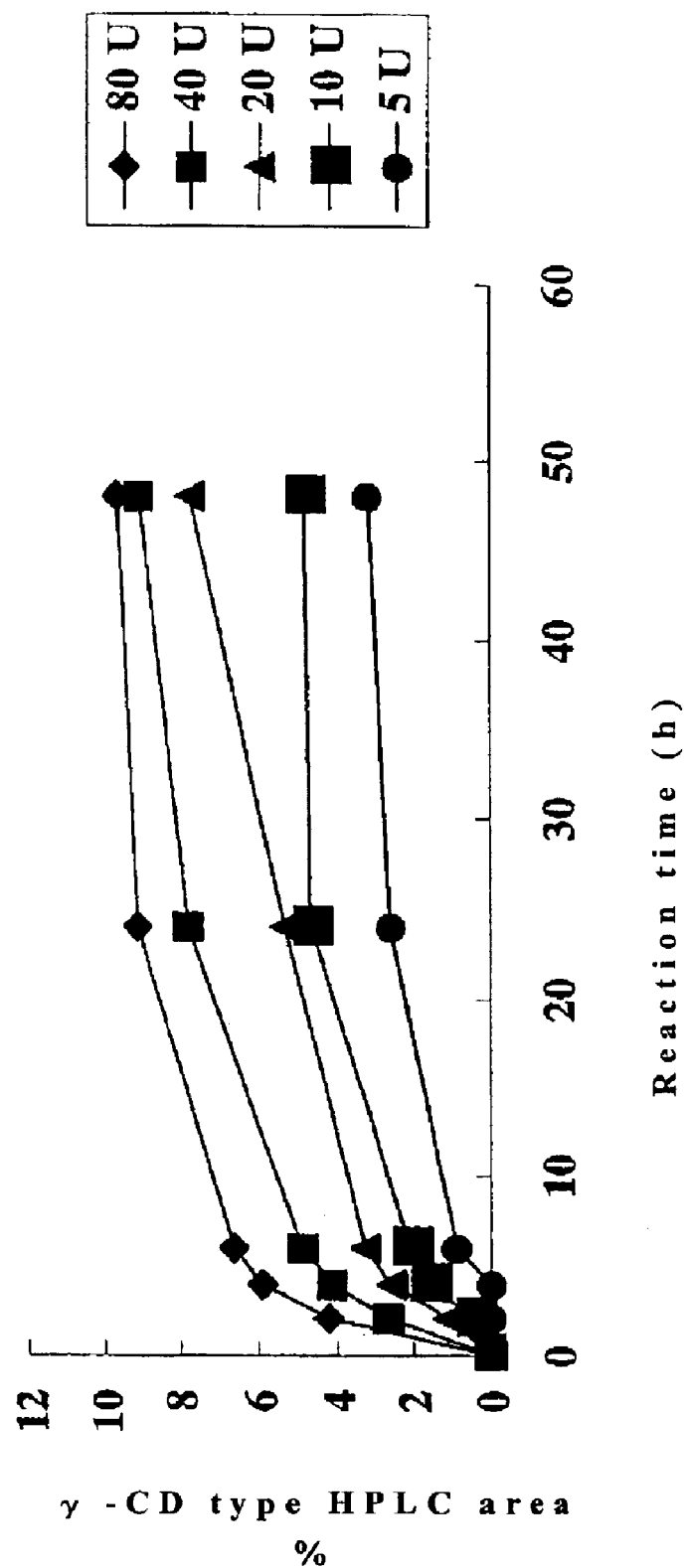
FIG. 3 is a graph showing change over time in the γ-CD production reaction using soluble starch as a substrate.

The culture supernatant solution obtained in Embodiment 1 was concentrated with a UF concentration membrane (PM-10) to obtain a crude enzyme solution and a saccharification test was conducted. The concentrated solution had an activity of 55 U/mL (Blue value method). A substrate solution was first prepared by dissolving a substrate in the form of soluble starch to 10 percent (w/v) in 50 mM glycine-NaCl—NaOH buffer (pH 10.0). The crude enzyme solution was then added in a manner yielding 80, 40, 20, 10, and 5 U/g-DS to 5 mL of the substrate solution and reacted at 50° C. Sampling was conducted at hours 2, 4, 6, 24, and 48 from the start of the reaction. HPLC Methods 1 and 2 were then employed to calculate the quantities of γ-CD produced (FIG. 3). The results revealed that when 80 U/g of DS was added, produced were 9.7 percent γ-CD, 1.7 percent α-CD, and 0.9 percent β-CD (HPLC area) in 48 hours.

Embodiment 3

Corn starch was liquefied by the usual method using α-amylase to prepare a liquid starch solution with a concentration of 20 weight percent and a glucose equivalent of 7. Next, the liquid starch solution was adjusted to pH 7. The culture supernatant solution described in Embodiment 1 was concentrated using an UF concentration membrane (PM-10) to obtain a crude enzyme solution, to which added 450 unit/g substrate and reacted for 48 hours at 55° C. Subsequently, the reaction solution was heated to deactivate the enzyme. Purification such as decoloration and ion-exchange were conducted to prepare a CD-comprising syrup. The sugar composition thereof is given in Table 3. The CD content was determined by HPLC Methods 1 and 2.

TABLE 3

| | |
|---|---|
| α-CD | 1.7 percent |
| β-CD | 0.8 percent |
| γ-CD | 8.2 percent |
| Other sugars | 89.3 percent |

Embodiment 4

The reaction solution of Embodiment 2 (a reaction solution to which 80 U/g of DS was added and reacted for 48 hours) was processed with glucoamylase, placed on an activated carbon column (φ2.5×20 cm), and washed with pure water to remove the glucose produced by glucoamylase processing. After further washing with 20 percent ethanol, adsorption fractions were eluted out with a threefold quantity of 25 percent ethanol. The eluted fractions were concentrated and then cooled for 15 min at 4° C. to precipitate β-CD, which was removed by centrifugation. Next, the supernatant was placed on Toyopal HW-40S (φ2.9×90 cm). When the Brix of each 10 mL fraction was measured, a single principal peak was observed (Tube: 23–28). Each fraction was analyzed by HPLC, revealing that fractions 23–26 were either α-CD or mixtures of α-CD and γ-CD. Thus, fractions 27 and 28 were collected, concentrated, and freeze dried. Determination by HPLC revealed that these fractions were γ-CD with a purity of 99.5 percent. Finally, 175 mg of γ-CD was isolated. This γ-CD was confirmed to be γ-CD by NMR.

$^{13}$C-NMR data: 104.30, 83.08, 75.56, 74.93, 74.40, 62.86 ppm.

INDUSTRIAL APPLICABILITY

The present invention provides a microorganism having the ability to produce a new γ-CGTase and a new γ-CGTase capable of predominantly producing γ-CD. The present invention further provides a method of efficiently manufacturing γ-CD using γ-CGTase.

What is claimed is:

1. Cyclodextrin glucanotransferase having the enzymatic chemical properties listed below:
   a) function and substrate specificity: enzymatically acting on starch, dextrin, amylopectin, and amylose to produce primarily γ-cyclodextrin, with the quantities of β- and α-cyclodextrin produced being smaller than the quantity of γ-cyclodextrin produced;
   b) optimum pH: 10.5–11.0;
   c) optimum temperature: about 60° C.;
   d) stable pH: 6–11;
   e) temperature stability: with a 15 minute-treatment at 50° C., residual activity of not less than 90 percent is exhibited.

2. A method of manufacturing cyclodextrin glucanotransferase wherein a microorganism belonging to the species *Bacillus clarkii* that produces cyclodextrin glucanotransferase is cultured to produce cyclodextrin glucanotransferase, and the cyclodextrin glucanotransferase that has been produced is collected.

3. The manufacturing method according to claim 2, wherein the microorganism belonging to the species *Bacillus clarkii* and having ability to produce cyclodextrin glucanotransferase is *Bacillus clarkii* strain 7364 (FERM BP-7156).

4. A method of manufacturing cyclodextrin wherein cyclodextrin glucanotransferase produced by the species *Bacillus clarkii* is reacted with a solution comprising at least one member selected from the group consisting of starch, dextrin, amylopectin, and amylose to produce principally γ-cyclodextrin.

5. The manufacturing method according to claim 4, wherein the cyclodextrin glucanotransferase having the enzymatic chemical properties listed below:
   a) function and substrate specificity: enzymatically acting on starch, dextrin, amylopectin, and amylose to produce primarily γ-cyclodextrin, with the quantities of β- and α-cyclodextrin produced being smaller than the quantity of γ-cyclodextrin produced;
   b) optimum pH: 10.5–11.0;
   c) optimum temperature: about 60° C.;
   d) stable pH: 6–11;
   e) temperature stability: with a 15 minute-treatment at 50° C., residual activity of not less than 90 percent is exhibited.

6. The manufacturing method according to claim 4, wherein the γ-cyclodextrin produced is separated from other cyclodextrins.

7. *Bacillus clarkii* strain 7364 (FERM BP-7156) being the species *Bacillus clarkii* having the ability to produce cyclodextrin glucanotransferase.

* * * * *